United States Patent
Ketchum

(10) Patent No.: US 7,322,359 B2
(45) Date of Patent: Jan. 29, 2008

(54) LEAK POINT WETNESS SENSOR FOR UROLOGICAL INVESTIGATIONS

(75) Inventor: Gary T. Ketchum, Newbury Park, CA (US)

(73) Assignee: SRS Medical Systems, Inc., North Billerica, MA (US)

( * ) Notice: Subject to any disclaimer, the term of this patent is extended or adjusted under 35 U.S.C. 154(b) by 858 days.

(21) Appl. No.: 09/788,274

(22) Filed: Feb. 16, 2001

(65) Prior Publication Data

US 2002/0112731 A1   Aug. 22, 2002

(51) Int. Cl.
*A61F 5/48* (2006.01)
(52) U.S. Cl. .......................................... 128/886; 600/29
(58) Field of Classification Search ................. 128/885, 128/886; 600/29–31
See application file for complete search history.

(56) References Cited

U.S. PATENT DOCUMENTS

| 3,818,468 | A | * | 6/1974 | Toth | 128/886 |
| 5,469,145 | A | * | 11/1995 | Johnson | 128/886 |
| 5,469,146 | A | * | 11/1995 | Gurler | 128/886 |
| 5,790,035 | A | * | 8/1998 | Ho | 128/886 |
| 5,862,804 | A | * | 1/1999 | Ketchum | 128/885 |

* cited by examiner

*Primary Examiner*—Michael A. Brown
(74) *Attorney, Agent, or Firm*—Cesari and McKenna, LLP

(57) ABSTRACT

A leak point wetness sensor for urological investigations. A receptacle receives liquid which leaks past a catheter inserted in the urethra. A temperature sensitive detector sensor is contacted by the leaked liquid and provides a signal output responsive to the temperature of the liquid. A circuit produces a reference output simulative of a temperature below the anticipated temperature of leaked liquid. A comparator produces a signal when the difference between the outputs is sufficient to confirm leakage.

18 Claims, 2 Drawing Sheets

LEAK POINT WETNESS SENSOR FOR UROLOGICAL INVESTIGATIONS

FIELD OF THE INVENTION

For use in urological investigations of the female bladder and urethra, a detector responsive to leakage of liquid from the urethra.

BACKGROUND OF THE INVENTION

Urologists and other physicians are interested in learning when and under what conditions leakage from urethra first occurs during an investigation of the bladder and urethra. In the course of the investigation, liquid is forced into the bladder through a catheter, and the pressure and the amount of liquid (urine and water) is known. The patient is asked to assume a number of positions, and to make various exertions, such as muscular contraction and coughing. In the course of these events, liquid will at times and under certain circumstances leak past the catheter. The conditions under which this leakage just begins is of importance to the physician in his investigation of the bladder and urethra.

While leakage can be visually detected, the relationship of its exact time of occurrence with respect to other measured parameters during a urodynamic procedure is critical for the proper evaluation of the test data. It is an object of this invention to provide a simple and rugged sensor and related circuity which will inform the urologist of the event of leakage, and if desired will also record the relative time and conditions under which it occurred, all without immediate attention by the physician.

A sensor to detect and notify of leakage past the urethra is disclosed in Ketchum U.S. Pat. No. 5,862,804, which does in fact detect such leakage, relying on a difference between ambient (room) temperature and the temperature of the leaked liquid. This instant invention, by the same inventor, is intended to provide optional or less complex references and measurements for the same purposes.

BRIEF DESCRIPTION OF THE INVENTION

A sensor according to this invention, including its reference and temperature responsive circuity, detects wetness by measuring the temperature of a liquid which contacts it. It is an advantage of this invention that the sensor responds quickly to the temperature of the liquid, but drains and dries quickly so as to be sensitive to next events, such as leakage caused by successive, relatively rapid coughs without being masked by the previous event.

It is an object of this invention to simplify the sensor system shown in the Ketchum patent in order to reduce its cost and also to reduce the number of comparative measurements which need to be made in order to detect the liquid.

In its every embodiment the sensor functions by sensing the temperature which is respective to liquid expelled from the urethra. It should be observed that this instrument surrounds a catheter which is inserted into the bladder through the urethra. The instrument is held immediately adjacent to the urethra. The liquid when it reaches the sensor will have leaked past the catheter and will be at or very near to body temperature. This temperature will invariably be higher than ambient, and higher than any other temperature likely to be encountered by the instrument.

Accordingly, in one embodiment of this invention, instead of using the output from a sensor responding to ambient temperature, a reference circuit provides a generated output simulative of some temperature sufficiently lower than the output of a sensor that is responsive to temperature of the liquid. Then only one sensor is needed. This can greatly simplify the instrument, and will reduce its cost and complexity.

In another embodiment of the invention, the rate of rise of the temperature where the liquid is to be detected can be used. A sufficient rate of rise would not be occasioned merely by a change in room temperature, which would be gradual. Instead it would be caused by contact with a warm liquid. A sufficient rate of rise will correctly reflect contact with a liquid at a sufficient temperature.

The above and other features of this invention will be fully understood from the following detailed description and the accompanying drawings, in which:

DETAILED DESCRIPTION OF THE INVENTION

Figure 3:
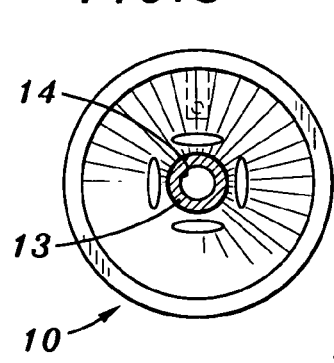
FIG. 3 is an end view taken at line 3-3 in FIG. 2.
Figure 2:
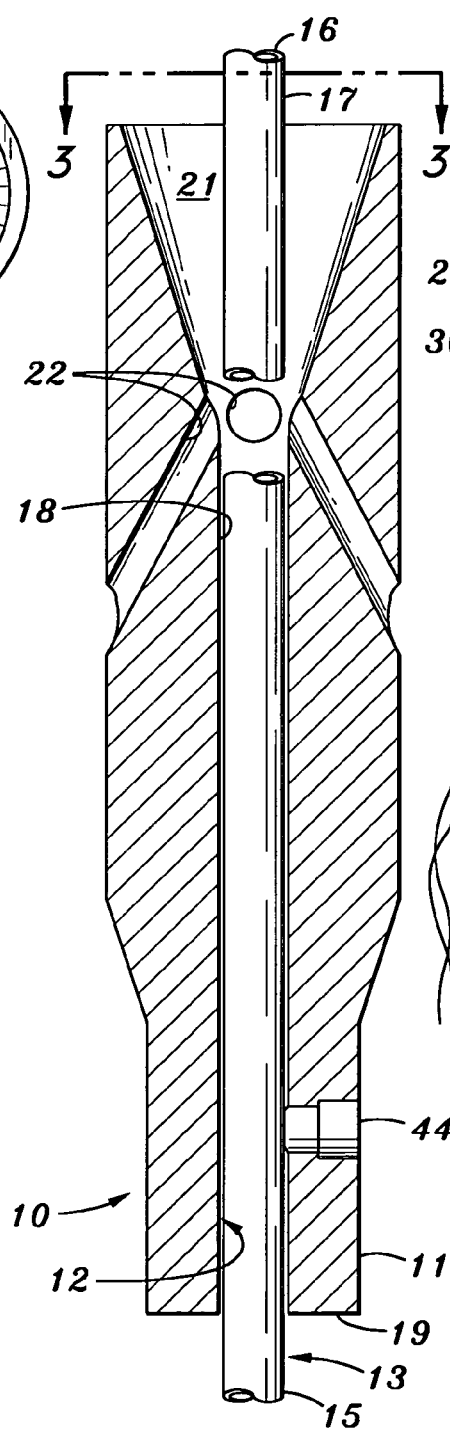
FIG. 2 is an axial cross-section taken at line 2-2 in FIG. 1.
Figure 1:
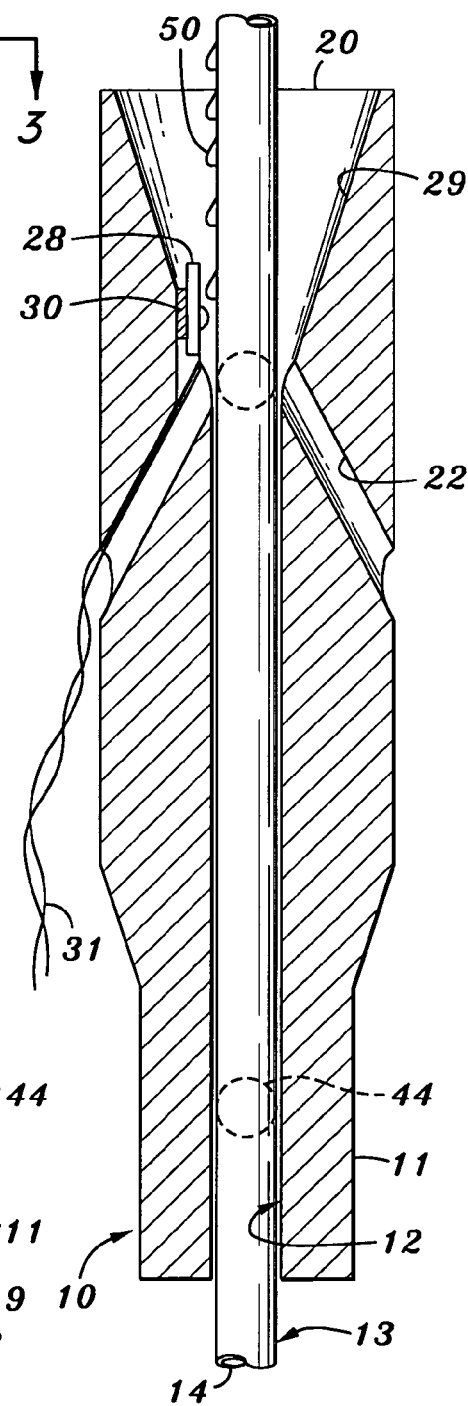
FIG. 1 is an axial cross-section of the preferred embodiment of a wetness sensor according to the invention.

A leak point detector 10 according to the invention is shown in FIGS. 1-3. Its body 11 may have any desired external configuration, from a simple cylindrical shape to one which is shaped for a better grip. A passage 12 passes a catheter 13.

The catheter is a tube having an internal lumen 14 through which liquid, usually water or a saline solution, is passed into the bladder. The proximal end 15 of the catheter is connected to a source of liquid (not shown). The distal end 16 of the catheter is passed through the urethra into the bladder. Leakage to be detected will flow between the urethral wall and the external wall 17 of the catheter when the urethra is no longer able to prevent the leakage.

Catheter wall 17 makes a close fit with wall 18 of passage 12 at its proximal end 19. Passage 12 is expanded at the distal end 20 of the body to form a receptacle 21. Drain channels 22 extend from the receptacle to the exterior of the body so as to drain liquid that flows into the receptacle. There is no intention or purpose to collect the liquid, and it must promptly be drained for a reason yet to be disclosed.

A temperature sensitive detector sensor 28 is bonded to the wall 29 of the receptacle by a layer 30 of cement. The detector is exposed so as to be contacted by liquid which has leaked from the patient. It is also exposed to ambient temperature through the drain channels.

Figure 4:
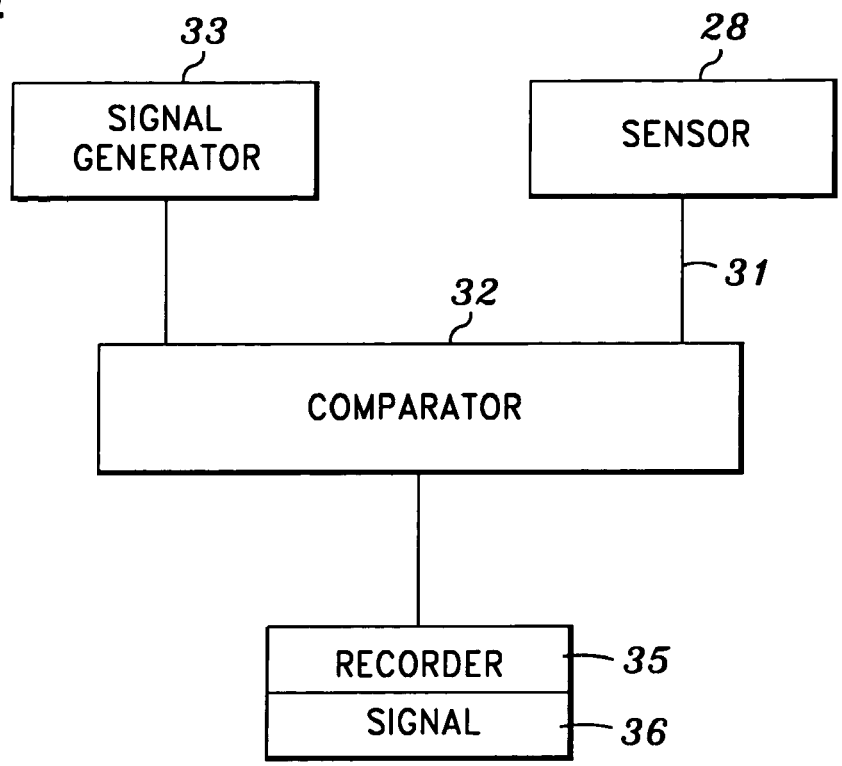
FIG. 4 is a schematic circuit drawing of another embodiment of the invention.

According to one embodiment of the invention, shown in FIG. 4, the signal from detector sensor 28 is provided through leads 31 to a comparator 32. This signal is, for example, a voltage proportional and respective to the temperature of the sensor-that is, the temperature measured of leaked liquid that contacts it. When dry, the signal merely reflects what is around it, usually ambient air. When wetted, it will be the temperature of the liquid expelled from the urethra, which will always be higher than ambient.

A circuit 33 acts as a signal generator which generates and provides a signal, usually a voltage, simulative of some lower temperature than would be expected from the liquid. It will usually be proportional to ambient. Its setting is preferably, but not necessarily adjustable, but it is not temperature responsive. Instead it is non-reactive and will ordinarily be set to produce a voltage respective to a simulated temperature somewhat greater than ambient, but less than that of leaked liquid. There always will be a difference between the two signals, so the comparator will be adjusted to provide no output signal of its own when the sensor is dry. Then, when the sensor is wetted by warm liquid, the comparator will have been set to respond when the sensor temperature increases by some arbitrary number of degrees above the simulated temperature, perhaps 10 degrees.

The signal from the comparator is provided to a recorder 35 and to a signal 36. Obtaining this signal is the objective. It states the event of leakage. The actual temperature of the leaked liquid is immaterial.

Figure 5:
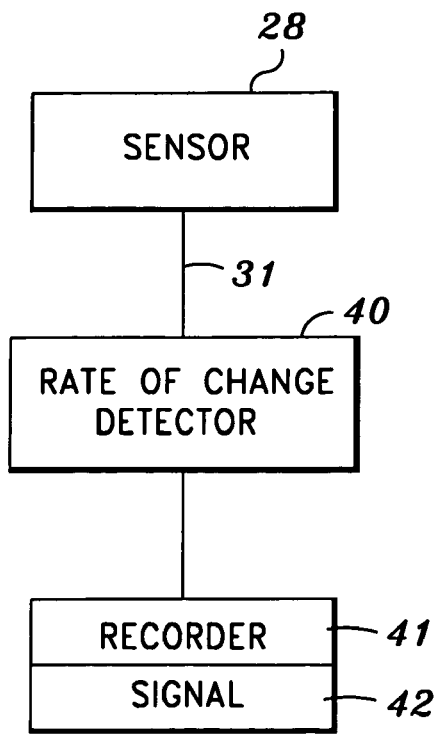
FIG. 5 is a schematic circuit drawing of yet another embodiment of the invention.

The second embodiment, shown in FIG. 5, does not respond to any specific temperature. Rather it responds to rate of change of temperature. Thus, gradual changes in room temperature, and changes in the temperature of the body of the instrument itself are ignored by it. However, when leaked liquid at an elevated temperature contacts the sensor, there will be a rapid rise of temperature at the sensor, which is uniquely indicative of the presence of the warm liquid.

For this purpose, the signal from detector sensor 28 is provided to a rate of change detector 40. This will react to a change of the sensor output respective to a quick rise in temperature. A typical differentiating circuit will perform this task, and no specific description is required for an understanding of the invention. A required rate of rise can readily be determined, and the detector can be adjusted to that level, both by brief observation of the existing circumstances. Detector 40 provides its signal to a recorder 41 and/or a signal 42. It stops its signal when the temperature falls, so as to be ready for the next liquid. It will be observed that there is no source of a simulated temperature for comparison purposes. No comparison is made. Only the abrupt rise occasioned by the leaked fluid is detected.

In the procedure, the catheter is first passed into the bladder through the urethra. Then to position the wetness sensor on the catheter, the proximal end of the catheter is either passed through the passage 12, or is clamped around the catheter depending on the particular design of the wetness sensor. In either case, when it is placed at a desired location along the catheter, a plunger 44, or other friction device will be set to bear against the catheter so the body cannot slide along the catheter. The plunger, or other friction device, may be spring-driven, threaded, or otherwise mounted as desired for this purpose.

A thermistor is the preferred example of a temperature sensing element for use in this device. Its surface is resistant to water and to urine, and it is sensitive to small changes of temperature. Its resistance decreases with increasing temperature. However, other types of temperature sensors, including direct-reading electronic thermometers may be used instead. Therefore the thermistor is referred to generally as a temperature sensitive element, but it is the preferred device.

In use, leakage liquid generally first flows slowly, drop-by-drop as shown in the FIG. 1 as drops 50. They flow along the surface of the catheter to the narrowed part of the receptacle, where they contact the detector sensor. Then they flow out through the drain channels so the thermistor can drain dry again and be ready for the next drops. It is undesirable for the detector thermistor to remain in continuous contact with the liquid, because this would frustrate the comparison between the temperature of freshly-received liquid and the ambient temperature, and would prevent intermittent flows from being sensed.

This invention is not to be limited by the embodiments shown in the drawings and described in the description, which are given by way of example and not of limitation, but only in accordance with the scope of the appended claims.

I claim:

1. A leak point wetness detector for urological investigations comprising:
    an instrument body having a passage therethrough to pass a catheter, which catheter is intended for insertion into the bladder through the urethra;
    a receptacle in said instrument body so arranged and disposed as to receive liquid which leaks from the urethra past the inserted catheter;
    a temperature sensitive detector sensor mounted to said instrument body where it will be contacted by said leaked liquid, said detector sensor being responsive to the temperature of said liquid and adapted to provide a signal output respective to said temperature;
    a signal generator to generate and provide a reference output signal simulative of a selected temperature, where the selected temperature is below that of an anticipated temperature of said leaked liquid, and where the output signal of the selected temperature remains constant and is independent of ambient temperature; and
    a comparator responsive to the difference between said outputs to detect and inform when the signal output sufficiently exceeds said reference output.

2. The sensor according to claim 1 in which drainage channels extend from said receptacle to the outside of said body to drain liquid from the receptacle.

3. The sensor according to claim 1 in which recorder means records related data when wetness is detected.

4. A leak point wetness detector for urological investigations comprising:
    an instrument body having a passage therethrough to pass a catheter, which catheter is intended for insertion into the bladder through the urethra;
    a receptacle in said instrument body so arranged and disposed as to receive liquid which leaks from the urethra past the inserted catheter;
    a single temperature sensitive detector sensor mounted to said instrument body where it will be contacted by said leaked liquid, said detector sensor being responsive to the temperature of said liquid and adapted to provide a signal output respective to said temperature;
    a rate of change detector to detect a rate of change in the signal output from said single temperature sensitive detector sensor, said detected rate of change corresponding to a rate of change in temperature at said detector sensor.

5. The sensor according to claim 1, wherein said comparator outputs a signal indicating that liquid has leaked from said urethra.

6. The sensor according to claim 4, wherein said rate of change detector generates a signal indicating that liquid has leaked from said urethra.

7. The sensor according to claim 4, wherein said rate of change detector differentiates said signal output from said temperature sensitive detector sensor.

8. A leak point wetness device for urological investigations comprising:
- an instrument body having a passage therethrough to pass a catheter, which catheter is intended for insertion into the bladder through the urethra;
- a temperature sensitive detector sensor mounted to said instrument body where it will be contacted by liquid which leaks from the urethra past the inserted catheter, said detector sensor being responsive to the temperature of said liquid and adapted to provide a signal output respective to said temperature;
- a signal generator to generate and provide a reference output simulative of a selected temperature below that of an anticipated temperature of said leaked liquid, said signal generator generating said reference output independent of ambient temperature; and
- a comparator responsive to the difference between said outputs to detect and inform when the signal output from said detector sensor sufficiently changes relative to said reference output.

9. A leak point wetness device for urological investigations comprising:
- an instrument body having a passage therethrough to pass a catheter, which catheter is intended for insertion into the bladder through the urethra;
- a single temperature sensitive detector sensor mounted to said instrument body where it will be contacted by liquid which leaks from the urethra past the inserted catheter, said detector sensor being responsive to the temperature of said liquid and adapted to provide a signal output respective to said temperature; and
- a comparator to detect when the signal output from said single detector sensor sufficiently changes relative to a reference signal that is independent of ambient temperature and simulative of a selected temperature below that of an anticipated temperature of said leaked liquid.

10. The device according to claim 9, further comprising:
means for signaling the event of a leakage when the signal output from said detector sensor sufficiently changes relative to said reference signal.

11. The device according to claim 9, further comprising:
a signal generator generating said reference signal that is independent of ambient temperature and simulative of a selected temperature below that of an anticipated temperature of said leaked liquid.

12. A leak point wetness device for urological investigations comprising:
- an instrument body having a passage therethrough to pass a catheter, which catheter is intended for insertion into the bladder through the urethra;
- a single temperature sensitive detector sensor mounted to said instrument body where it will be contacted by liquid which leaks from the urethra past the inserted catheter, said detector sensor being responsive to the temperature of said liquid and adapted to provide a signal output respective to said temperature; and
- a rate of change detector to detect a rate of change in the signal output from said single temperature sensitive detector sensor, said detected rate of change corresponding to a rate of change in temperature at said single detector sensor.

13. The detector according to claim 4, further comprising a recorder that records a signal when the rate of change detector detects the single temperature sensor is greater then a preset threshold.

14. The detector according to claim 4, further comprising a signal when the rate of change detector detects the single temperature sensor is greater then a preset threshold.

15. A leak point wetness device for urological investigations comprising:
- an instrument body having a passage therethrough to pass a catheter, which catheter is intended for insertion into the bladder through the urethra;
- a single temperature sensitive detector sensor mounted to said instrument body where it will be contacted by liquid which leaks from the urethra past the inserted catheter, said detector sensor being responsive to the temperature of said liquid and adapted to provide a signal output respective to said temperature;
- a signal generator to generate and provide a reference output simulative of a selected temperature below that of an anticipated temperature of said leaked liquid; and
- a comparator responsive to the difference between said output from signal generator and said output from the single temperature sensitive detector sensor, where the comparator detects and informs when the signal output from said single detector sensor sufficiently changes relative to said reference output.

16. The device according to claim 15, further comprising:
a recorder that stores when the comparator detects when the signal output from said single detector sensor sufficiently changes relative to said reference output.

17. The device according to claim 15, wherein said reference output independent of ambient temperature.

18. The device according to claim 15, wherein said reference output independent of environmental conditions.

* * * * *